United States Patent [19]

Nikander et al.

[11] Patent Number: 5,438,048
[45] Date of Patent: Aug. 1, 1995

[54] METHYLENEBISPHOSPHONIC ACID DERIVATIVES

[75] Inventors: Hannu Nikander, Paattinen; Marjaana Heikkilä-Hoikka, Vanhalinna; Esko Pohjala, Tampere; Hannu Hanhijärvi; Leena Laurén, both of Turku, all of Finland

[73] Assignee: Leiras Oy, Turku, Finland

[21] Appl. No.: 78,157

[22] PCT Filed: Dec. 18, 1991

[86] PCT No.: PCT/FI91/00394

§ 371 Date: Oct. 20, 1993

§ 102(e) Date: Oct. 20, 1993

[87] PCT Pub. No.: WO92/11267

PCT Pub. Date: Sep. 7, 1992

[30] Foreign Application Priority Data

Dec. 20, 1990 [FI] Finland .................. 906294

[51] Int. Cl.⁶ .................................... A61K 31/66
[52] U.S. Cl. .................................... 514/108; 556/405; 558/155; 558/158; 558/159; 558/160; 558/161
[58] Field of Search ............... 558/155, 158, 161; 514/108

[56] References Cited

U.S. PATENT DOCUMENTS

| | | | |
|---|---|---|---|
| 3,202,579 | 8/1965 | Berth et al. | 8/406 |
| 3,303,139 | 2/1967 | Blaser . | |
| 3,683,080 | 8/1972 | Francis . | |
| 3,904,493 | 9/1975 | Losi et al. | 558/161 X |
| 3,957,858 | 5/1976 | Kerst . | |
| 3,962,318 | 6/1976 | Kerst | 562/21 |
| 4,113,861 | 9/1978 | Fleisch et al. | 514/102 |
| 4,309,364 | 1/1982 | Bentzen et al. | 558/163 |
| 4,634,691 | 1/1987 | Hedglin . | |
| 4,645,762 | 2/1987 | Biere et al. . | |
| 4,818,774 | 4/1989 | Kern | 558/161 X |
| 4,927,814 | 5/1990 | Gall et al. | 514/108 |
| 4,942,157 | 7/1990 | Gall et al. . | |

FOREIGN PATENT DOCUMENTS 0054663 7/1981 Australia .
1617118 2/1971 Germany .

OTHER PUBLICATIONS

Xiao, Z. et al., *Chem. Abstr.*, 1992, 116(19), 194590; CN 1044281, publ. Aug. 1, 1990.

*Primary Examiner*—Robert W. Ramsuer
*Assistant Examiner*—Michael G. Ambrose
*Attorney, Agent, or Firm*—Wolf, Greenfield & Sacks

[57] ABSTRACT

Novel pharmacologically active methylenebisphosphonates having formula (I) wherein $R^1$, $R^2$, $R^3$ and $R^4$ independently are straight or branched, optionally unsaturated $C_1$–$C_{10}$-alkyl, optionally unsaturated $C_3$–$C_{10}$-cycloalkyl, aryl, aralkyl, silyl $SiR_3$ or hydrogen, whereby in formula (I) at least one of the groups $R^1$, $R^2$, $R^3$ or $R^4$ is hydrogen and at least one of the groups is different from hydrogen, $Q^1$ is hydrogen, hydroxyl, halogen, amino $NH_2$, or $OR'$, wherein $R'$ is $C_1$–$C_4$-lower alkyl or acyl, $Q^2$ is straight or branched, optionally unsaturated $C_1$–$C_{10}$-alkyl, -hydroxyalkyl or -aminoalkyl, whereby the oxygen may, as a substituent, contain one group or the nitrogen as a substituent may contain one or two groups, which are $C_1$–$C_4$-lower alkyl or acyl, or the two substituents of the nitrogen form together with the nitrogen atom a saturated, partly saturated or an aromatic heterocyclic ring, or $Q^2$ is optionally substituted and optionally unsaturated $C_3$–$C_{10}$-cycloalkyl, which optionally is bound to the molecule over a straight or branched alkylene group containing 1–4 C-atoms, including the stereoisomers, such as the geometrical isomers and the optically active isomers, of the compounds, as well as the pharmacologically acceptable salts of these compounds.

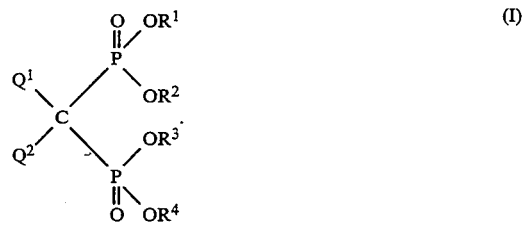

(I)

4 Claims, No Drawings

METHYLENEBISPHOSPHONIC ACID DERIVATIVES

This application was filed under 35 USC 371 and is based upon PCT International Application PCT/IJ 91/00394 which was filed on Dec. 18, 1991.

The invention concerns novel methylenebisphosphonic acid derivatives, in particular novel alkyl or aminoalkyl substituted methylenebisphosphonic ester acids and ester salts, processes for the preparation of these novel compounds, as well as pharmaceutical compositions comprising these novel compounds.

Several publications disclose methylenebisphosphonic acids, their salts and some tetraesters, but there are only a few disclosures of corresponding partial esters, tri-, di- and monoesters.

The preparation of tetraesters of methylenebisphosphonic acids has been described in the publications: EP 0221 611; J. Am. Chem. Soc. 78, (1956) 4450; J. Chem. Soc. (1959) 2266 and 2272; J. Am. Chem. Soc. 84 (1962) 1876; J. Org. Chem. 35, (1970) 3149; J. Org. Chem. 36, (1971) 3843 and Phosphorus, Sulfur and Silicon 42, (1989) 73.

According to the invention it has been discovered that the novel partial esters of substituted methylenebisphosphonic acids and their salts in many cases exhibit more favourable properties than the corresponding bisphosphonic acids and salts due to their better kinetics and availability, their ability to participate as complex formers in the regulation of the metabolism of the organism being maintained.

They are well suited for the treatment of disorders relating to the metabolism of calcium and of other, especially bivalent metals. They may be used both for the treatment of diseases in the skeletal system, especially of bone formation and resorption disorders, such as of osteoporosis and Paget's disease, as well as for the treatment of diseases in the soft tissues, such as of deposition and mineralisation conditions and bone formation disorders.

On the other hand, being pyrophosphate analogs, the new substituted methylenebisphosphonic acid derivatives are also suitable for the treatment of disorders in the (pyro)phosphate functions of the organism, including the functions, wherein an active, but disturbance-prone or wrongly active organic part is attached to (pyro)phosphate or acts as a metal complex or a combination of the last mentioned.

The novel bisphosphonates regulate either directly or over an indirect mechanism the quality and level of cations and/or pyrophosphate compounds freely present in the body fluids as well as of that binding to, active in and liberated from the tissues. Thus they are able to regulate the cellular metabolism, growth and destruction. Consequently they are useful for the treatment of e.g. cancer of the bone and metastases thereof, ectopic calcifications, urolithiasis, rheumatoid arthritis, bone infections and bone degradation.

Typical for the novel substituted methylenebisphosphonates is a selective desired and controlled action, providing for a better therapeutic index.

The invention concerns novel methylenebisphosphonic acid derivatives of the general formula I

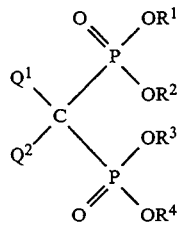

in which formula $R^1$, $R^2$, $R^3$ and $R^4$ independently are straight or branched, optionally unsaturated $C_1$–$C_{10}$-alkyl, optionally unsaturated $C_3$–$C_{10}$-cycloalkyl, aryl, aralkyl, silyl $SiR_3$ or hydrogen, whereby in the formula I at least one of the groups $R^1$, $R^2$, $R^3$ and $R^4$ is hydrogen and at least one of the groups $R^1$, $R^2$, $R^3$ and $R^4$ is different from hydrogen, $Q^1$ is hydrogen, hydroxyl, halogen, amino $NH_2$, or $OR'$, wherein $R'$ is $C_1$–$C_4$-lower alkyl or acyl, $Q^2$ is straight or branched, optionally unsaturated $C_1$–$C_{10}$-alkyl, -hydroxyalkyl or -aminoalkyl, whereby the oxygen may, as a substituent, contain one group or the nitrogen as a substituent may contain one or two groups, which are $C_1$–$C_4$-lower alkyl or acyl, or the two substituents of the nitrogen form together with the nitrogen atom a saturated, partly saturated or an aromatic heterocyclic ring, or $Q^2$ is optionally substituted and optionally partly unsaturated $C_3$–$C_{10}$-cycloalkyl, which optionally is bound to the molecule over a straight or branched alkylene group containing 1–4 C-atoms, including the stereoisomers, such as the geometrical isomers and the optically active isomers, of the compounds, as well as the pharmacologically acceptable salts of the compounds.

The groups $R^1$, $R^2$, $R^3$ and $R^4$ are independently a straight or branched alkyl, alkenyl or alkynyl group and they contain 1 to 10, respectively 2 to 10 carbon atoms, preferably 1 to 7, respectively 2 to 7, and advantageously 1 to 4, respectively 2 to 4 carbon atoms.

Optionally unsaturated cycloalkyl is cycloalkyl or cycloalkenyl with 3 to 10 C-atoms, preferably, however, cyclopropyl, -butyl, -pentyl, or -hexyl.

Aryl or aralkyl mean optionally $C_1$–$C_4$-lower alkyl, -lower alkoxy or halogen substituted monocyclic aryl or aralkyl, such as phenyl and benzyl, preferably, however, unsubstituted phenyl or benzyl.

In the silyl group $SiR_3$ the group R is lower alkyl containing 1 to 4 carbon atoms, and is especially methyl, ethyl, isopropyl, butyl, tert-butyl, or it is phenyl or R-substituted phenyl, whereby also different combinations of lower alkyls and phenyls come into question, such as dimethyl tert-butyl, methyl diisopropyl, dimethyl phenyl, diethyl phenyl, methyl tert-butyl phenyl, diisopropyl(2,6-dimethyl phenyl).

The group $Q^2$ contains as the alkyl, alkenyl and alkynyl group, hydroxy- or aminoalkyl, -alkenyl or -alkynyl group 1 to 10, respectively 2 to 10, preferably, however, 1 to 4, respectively 2 to 4, carbon atoms. As the substituent of the oxygen of the hydroxy group there may be one, and as the substituent of the nitrogen of the amino group there may be one or two $C_1$–$C_4$-lower alkyl groups or acyl groups, or two substituents may, together with the nitrogen atom, form a heterocyclic, optionally substituted (e.g. $C_1$–$C_4$-alkyl), either saturated or an aromatic ring, which is, for example, morpholinyl, thiomorpholinyl, piperidinyl, piperazinyl, azetidinyl, pyrrolidinyl, and as an aromatic or partly hydrogenated group, pyrrolyl, imidazolyl, triazolyl, oxazolyl, thiazolyl, or as partly hydrogenated pyridyl, pyrimidyl, pyrazinyl, pyridazinyl, or azepinyl. Preferably it contains 3 to 6 ring atoms, and especially it is a pyrrolidino or piperidino group, or a phthalimido group.

Acyl may be alkyl-, aryl- or arylalkylcarbonyl, but also alkoxy-, aryloxy- or aralkoxycarbonyl, wherein alkyl contains 1 to 4 C-atoms and aryl has the meaning given above. Halogen means chlorine, bromine, fluorine or iodine.

Cycloalkyl and -alkenyl as the group $Q^2$ contain 3 to 10 carbon atoms, preferably cyclopropyl, -butyl, -pentyl, -hexyl, -heptyl, more preferably cyclopentyl or cyclohexyl, and they may be unsubstituted or substituted with (1–4C)-alkyl. It may be bicyclic, preferably bicyclo[3.2.0] or -[2.2.1]heptyl, -[4.2.0]- or -[3.2.1]octyl, -[3.3.1]nonyl or corresponding spiro hydrocarbon residue, as well as the corresponding cycloalkenyl group or unsaturated spiro structure, or it may be polycyclic, such as adamantyl.

Salts of the compounds of the formula I are especially their salts with pharmaceutically acceptable bases, such as metal salts, for example alkalimetal salts, especially litium, sodium and potassium salts, alkaline earth metal salts, such as calcium or magnesium salts, copper, aluminium or zinc salts, as well as ammonium salts with ammonia or with primary, secondary and tertiary, both aliphatic and alicyclic as well as aromatic amines, and quaternary ammonium salts, such as halides, sulphates and hydroxides, salts with aminoalcohols, such as ethanol-, diethanol- and triethanolamines, tris(hydroxymethyl)aminomethane, 1- and 2-methyl- and 1,1-, 1,2- and 2,2-dimethylaminoethanols, N-mono- and N,N-dialkylaminoethanols, N-(hydroxymethyl- and ethyl)-N,N-ethanediamines, as well as amino crown ethers and cryptates, and heterocyclic ammonium salts, such as azetidinium, pyrrolidinium, piperidinium, piperazinium, morpholinium, pyrrolium, imidazolium, pyridinium, pyrimidinium, quinolinium, etc., salts.

Especially good results have been obtained with the following mono- or dimethyl-, mono- or diethyl-, mono- or diisopropyl- esters, or corresponding mixed diesters, wherein $Q^1$ is hydroxy and $Q^2$ is lower alkyl, for example methyl, ethyl, propyl, isopropyl, 2,2-dimethylpropyl or butyl, or cyclohexyl, or 2-hydroxyethyl, 3-hydroxypropyl, 2-aminoethyl, 3-aminopropyl, (3-dimethylamino)propyl, [3-methyl(pentyl)amino]propyl, 5-aminopentyl.

Examples of such compounds are:
(1-Hydroxyethylidene)bisphosphonic acid monomethyl and monoethyl ester
(1-hydroxypentylidene)bisphosphonic acid monomethyl ester,
(1-hydroxyethylidene)bisphosphonic acid dimethyl and diethyl ester,
(2,2-dimethyl-1-hydroxypropylidene)bisphosphonic acid monomethyl ester
[hydroxy(cyclohexyl)methylidene]bisphosphonic acid monomethyl ester,
(1,2-dihydroxyethylidene)bisphosphonic acid dimethyl ester,
(1,3-dihydroxypropylidene)bisphosphonic acid monoethyl ester,
(3-amino-1-hydroxypropylidene)bisphosphonic acid monomethyl and monoethyl ester,
(4-amino-1-hydroxybutylidene)bisphosphonic acid monomethyl and monoethyl ester,
(6-amino-1-hydroxyhexylidene)bisphosphonic acid monomethyl- and monoisopropyl ester,
(3-amino-1-hydroxypropylidene)bisphosphonic acid P,P'-dimethyl and P,P'-diethyl ester,
(4-amino-1-hydroxybutylidene)bisphosphonic acid P,P'-dimethyl- and P,P'-diethyl ester,
[(4-dimethylamino)-1-hydroxybutylidene]bisphosphonic acid monoethyl ester, and
[(3-methyl(pentyl)amino]-1-hydroxypropylidene]bisphosphonic acid monomethyl ester.

The invention concerns also processes for the preparation of the compounds of the formula I, which is characterized in that a) a methylenebisphosphonic acid tetraester of the formula) II

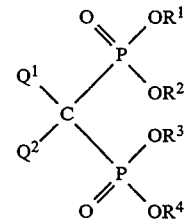

in which formula $Q^1$ and $Q^2$ have the same meaning as above, and $R^1$, $R^2$, $R^3$ and $R^4$ have the same meaning as above, except hydrogen, is selectively hydrolysed to a triester corresponding to the formula I, wherein one of the groups $R^1$, $R^2$, $R^3$ and $R^4$ has the meaning of hydrogen, or a salt thereof, or to a diester corresponding to the formula I, wherein two of the groups $R^1$, $R^2$, $R^3$ and $R^4$ have the meaning of hydrogen, or a salt thereof, or to a monoester corresponding to the formula I, wherein three of the groups $R^1$, $R^2$, $R^3$ and $R^4$ have the meaning of hydrogen, or a salt thereof, or b) a bisphosphonic acid of the formula

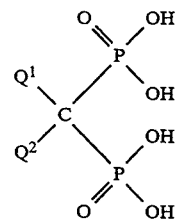

VII or a metal or ammonium salt thereof, or the corresponding acid tetrachloride, wherein $Q^1$ and $Q^2$ have the same meaning as above, is esterified selectively by reacting the same with an esterification reagent corresponding to the desired groups $R^1$, $R^2$, $R^3$ and $R^4$, to a monoester corresponding to the formula I, wherein three of the groups $R^1$, $R^2$, $R^3$ and $R^4$ have the meaning of hydrogen, or to a diester corresponding to the formula I, wherein two of the groups $R^1$, $R^2$, $R^3$ and $R^4$ have the meaning of hydrogen, or to a triester corresponding to the formula I, wherein one of the groups $R^1$, $R^2$, $R^3$ and $R^4$ has the meaning of hydrogen, or to the corresponding ester salts of the said partial esters, or c) a phosphonate having the formula

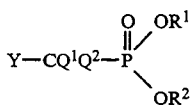

is reacted with an activated phosphate or a hydrogen phosphonate corresponding to the formula X

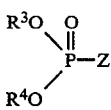

wherein in the formulas Y is hydrogen, hydroxy or halogen or other leaving group, Z is hydrogen, halogen, acyloxy, sulphonyloxy, alkoxy or aryloxy, and $R^1$ to $R^4$ and $Q^1$ and $Q^2$ have the same meaning as before, or $Q^1$ and $Q^2$ form a double-bonded oxygen or an imino group, or is reacted with a phosphite corresponding to the formula X, or d) a bisphosphonate corresponding to the formula I, which instead of $Q^2$ has a carbanion site, is reacted with ω-leaving group substituted $Q^2$, or a bisphosphonate corresponding to the formula I, which instead of $Q^2$ contains a leaving group, is reacted with a ω-carbanion corresponding to $Q^2$, or a ($Q^2$-$C_1$)-ω-carbanion is added by Michael addition in alkylidenebisphosphonates, or e) a bisphosphonite compound having the formula

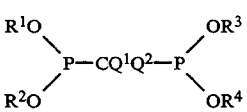

wherein $R^1$, $R^2$, $R^3$ and $R^4$ and $Q^1$ and $Q^2$ have the same meaning as in the formula I, or the corresponding hydrogen phosphonate compound, is oxidized to a compound of the formula I, and if desired, the partial ester acids obtained according to a) to e) are converted to partial ester salts, or the partial ester salts obtained are converted to the partial ester acids, and/or, if desired, a compound according to the formula I obtained is converted into some other compound according to the formula I by hydrolyzing, esterification or transesterification, and/or in a compound of the formula I, a group $Q^1$ is converted into another group $Q^1$ within the scope of the definition.

According to one process the compounds are thus prepared by selective hydrolysis of the tetraesters corresponding to the formula I. Thus a tetraester is used as the starting material, wherein the groups $R^1$ to $R^4$ and $Q^1$ and $Q^2$ have the same meaning as above and this tetraester is hydrolyzed stepwise to the triester III, diester IV and V and the monoester VI. If necessary, the partial ester or its salt may be isolated and purified by extraction, fractional crystallization or chromatographically, and if desired, a free acid may be converted into a salt or a salt into the free acid.

This reaction is shown in the appended scheme 1 (the reaction takes place in the direction of the upper arrow).

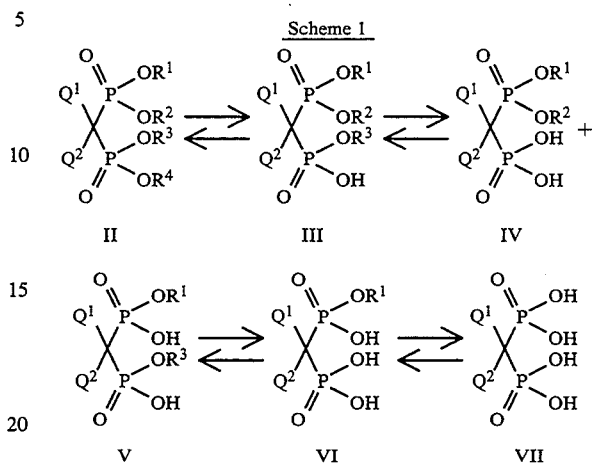

Scheme 1

The hydrolysis of the tetraesters II may be carried out by treating both with an acid and a base, using thermal cleaving, and in certain cases also using water, alcohols, or other neutral or non-neutral transalkylation, -silylation or -arylation reagents. The hydrolysis takes place advantageously at a temperature range of 10° to 150° C. The acids are advantageously conventional inorganic acids, such as hydrochloric acid, sulphuric acid, phosphoric acid, and Lewis acids, such as borotrifluoride etherate, titanium tetrachloride, etc., as well as a number of organic acids, such as oxalic acid, formic acid, acetic acid and other carboxylic acids, methanesulphonic acid and other sulphonic acids, such as tosyl acid, further chlorine and fluorine substituted carboxylic and sulphonic acids, such as trichloroacetic acid and trifluoromethane sulphonic acid, and their aqueous solutions.

The bases are advantageously alkali and ammoniumhydroxides and ammonia and the aqueous solutions thereof, as well as a number of amines, such as primary, secondary and tertiary amines, such as e.g. diethyl-, triethyl-, diisopropyl- and tributylamine, aniline, N- and N,N-alkyl substituted anilines and heterocyclic amines, such as pyridine, morpholine, piperidine, piperazine etc., and hydrazines, such as N,N-dimethyl hydrazine.

In addition, acids and bases bound to a solid substrate may be used, such as Amberlites, either in the presence of an organic solvent or water or various solvent mixtures, or in the absence thereof.

Further by treating with certain alkalimetals, such as sodium and litium, or with suitable inorganic salts, such as with sodium iodide, litium bromide, ammonium chloride and NaBr/PTC, the ester group may be converted to its corresponding salt, such as to the sodium, ammonium and litium salt.

Thermal cleaving usually takes place at a temperature of about 100° to 400° C., usually, however, at a temperature of not more than 250° C. The presence of a suitable catalyst, such as an acid or an acid solution, or a quaternary ammonium salt, makes it possible for a reaction to take place faster and at a lower temperature. Certain active substituents, such as benzyl and allyl, may be removed by catalytic reduction or electrolytically.

To improve solubility and to control the reaction temperature during the reactions, organic, inert solvents, such as hydrocarbons, lower alcohols and stable ketones and esters, alkyl halides, such as chloroform, dichloromethane and -ethane, ethers, such as dioxan, dimethoxyethane, diglyme, acetonitrile, etc., may be used as co-solvents.

When the groups $R^1$ to $R^4$ in the tetraester according to the formula II are the same, the hydrolysis takes place stepwise, and it is interrupted when the concentration of the desired partial ester is at its greatest.

In order to prepare a specific partial ester structure, it is advantageous to use a tetraester of the formula II wherein the ester groups are not the same, but groups which are different with respect to the hydrolysis rate. It has, for example, been discovered that the hydrolysis rate of alkyl and silyl esters is dependant on the structure as follows:

sily > tert > sec > prim

It is possible to affect the hydrolysis rate by changing also the size and shape of the alkyl and silyl substituent as well as by electronical factors. It is often possible to perform a transesterification in order to change the stepwise hydrolysis of the different ester sites. Especially the methyl ester may be advantageously converted to the corresponding acid over a silyl ester.

Pure partial esters may thus be prepared in an advantageous manner by performing a selective hydrolysis of mixed esters of the formula I, which have been prepared using ester groups which are advantageous from the point of view of hydrolysis.

Also other selective hydrolysis reactions known especially from phosphate and monophosphonate chemistry may be used.

The progress of the hydrolysis may be followed for example chromatographically or by means of $^{31}$P-NMR spectroscopy. The reaction may be interrupted when the level of the desired partial ester is at its greatest and the product may be isolated from the reaction mixture either as the free acid or as a salt by precipitation, extraction or chromatographically, and the salt form may be converted to the free acid or the free acid to its salt.

The compounds according to this invention may be prepared also by selective esterification of bisphosphonic acids in accordance with the above mentioned reaction Scheme 1 (the reaction takes place in the direction of the lower arrow).

A tetraacid according to the formula VII ($R^1$ to $R^4$=H) may thus be as a starting material used, which can be as the free acid or is in the form of a salt, such as a metal or ammonium salt, or the corresponding phosphonic acid tetrachloride may be used, and depending on the desired end result, 1 to 4 equivalents of the desired aliphatic or aromatic alcohol, or the corresponding activated alkylation, silylation and arylation reagents, such as ortoesters, ketene acetals and other suitable transfer reagents for alkyl-, silyl- and aryl groups, such as diazo compounds, active carboxylic acid esters, sulphates, etc. The reaction is usually performed under anhydrous conditions, preferably in the temperature range of 0° to 150° C., or when using an inert co-solvent, at the boiling point thereof.

The esters II to IV may also be prepared in a nucleophilic substitution reaction between the bisphosphonate anion, often the ammonium salt, and an organic halide or sulphonate, or in a condensation reaction between a phosphonic acid group and a suitable alcohol or a phenol using a reagent for cleaving off water, such as carbodiimides.

Pure partial esters, also mixed esters, may thus be prepared by selective esterification, if necessary stepwise, of tetraacids of the formula VII. Also other selective esterification reactions may be used known primarily from phosphate and monophosphonate chemistry.

The progress of the esterification reactions may be followed, for example, chromatographically or using $^{31}$P-NMR and the reaction is interrupted when the content of the desired partial ester is at its greatest and this is isolated from the reaction mixture by precipitation, extraction or chromatographically and, if desired, a salt form obtained is converted to the free acid or the free acid is converted to its salt.

Partial esters according to the invention may also be prepared by constructing the P-C-P frame from its parts

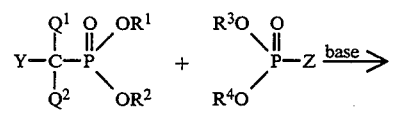

wherein in the formula Y is hydrogen, hydroxy or halogen or other leaving group, Z is halogen, acyloxy, sulphonyloxy, alkoxy, or aryloxy, and $R^1$ to $R^4$ and $Q^1$ and $Q^2$ have the meaning given above, or $Q^1$ and $Q^2$ are double-bonded oxygen or an imino group. As the base, for example, sodium hydride, butyl litium or litium diisopropylamide may be used. In the starting material optionally present free acid sites (one of the groups $R^1$ to $R^4$=H) have to be neutralized, by using a sufficient amount of base, prior to the coupling reaction. Also active sites in the groups $Q^1$ and $Q^2$ have to be neutralized or the said active site has to be protected with a protecting group.

Also the Michaelis-Arbuzov reaction may be used, whereby the second reacting compound is a phosphite, or the Michaelis-Becker reaction, whereby Z is hydrogen.

In certain instances the group $Q^1$ may be introduced by an exchange reaction, or an oxidation or reduction reaction, whereby hydroxyl may be obtained from hydrogen, halogen or amino, the amino group may be obtained from halogen or hydroxyl and hydrogen may be obtained from halogen, and halogen may be obtained from hydrogen.

$Q^2$ may also be brought into the molecule either by a reaction of a bisphosphonate carbanion or corresponding reaction involving C-halogen or other leaving group, whereby the $Q^2$-reagent is ω-substituted with a leaving group, or correspondingly is a ω-carbanion.

The compounds according to the invention may also be prepared by applying the Michael addition to alkylidene phosphonates described in the EP patent application 0 221 611.

The esters according to the invention may also be prepared from P-C-P-structures at a lower oxidation level by oxidation

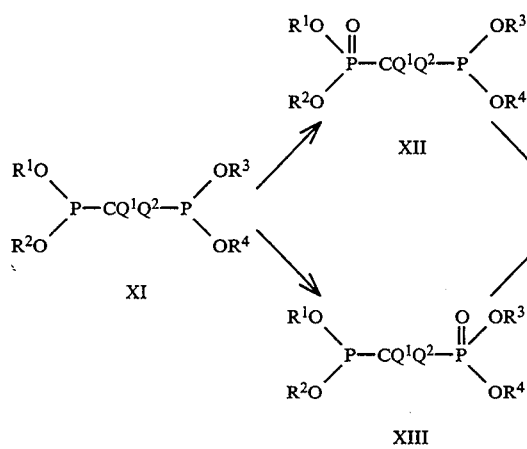

TABLE 1

Effect of bisphosphonates and their derivatives on hydroxyapatite

| Compound | Binding, Ki μm | Inhibition of growth |
|---|---|---|
| Clodronate | 1.3 | +++ |
| Etidronate | 0.9 | |
| (1-Hydroxypentylidene)-bisphosphonate | 2.5 | +++ |
| Monoisopropyl-(1-hydroxyethylidene)bisphosphonate | 7.3 | +++ |
| Monoisopropyl-(1-hydroxypentylidene)bisphosphonate | 15.4 | ++ |
| Monomethyl-(1-hydroxypentylidene)bisphosphonate | 11.8 | +++ |

+++ = complete inhibition at 100 μM
++ = almost complete inhibition at 100 μM
+ = slight inhibition at 100 μM.

TABLE 2

Antiresorptive acitivity
Inhibition of resorption (%)

| | 100 μm in vitro | 1000 μm | 150 μmole/kg in vivo |
|---|---|---|---|
| Clodronate | 43 | ND | 64 |
| (1-Hydroxypentylidene)-bisphosphonate | 56 | ND | ND |
| Monomethyl-(1-hydroxypentylidene)bisphosphonate | 7 | 47 | 52 |

ND = Not determined.

whereby in the formulas $R^1$ to $R^4$ and $Q^1$ and $Q^2$ have the same meaning given above, and whereby the phosphonite structure may exist in an equilibrium with the hydrogenphosphonate structure. All conventional oxidation agents, or their solutions, such as hydrogen peroxide, perhalogen compounds, peracids, permanganate etc., come into question.

The partial esters of bisphosphonic acid according to the invention may also be prepared from other partial esters by performing an intra- or intermolecular exchange reaction.

The tetraesters II and corresponding tetraacids IV used as starting materials in the above reactions may be prepared by processes known as such from literature by constructing the P-C-P frame from its parts, for example using the above mentioned Michaelis-Becker-, Michaelis-Arbuzov- or carbanion reaction, also stepwise, whereby the groups $R^1$ to $R^4$ may be chosen and advantageously introduced as parts of the bisphosphonate taking into account the structure of the desired partial ester, and by suitably substituting this frame or an anion obtained therefrom, for example by an alkylation or an addition reaction.

Taking into account the preparation of a desired partial ester, the prepared tetraesters may, if necessary, be converted to other suitable tetraesters using exchange reactions. Thereby the groups $OR^1$ to $OR^4$ may be exchanged directly or over the corresponding phosphono-chloride or by applying other known processes.

Optically active partial esters may be best prepared by using known optically active compounds, such as optically active alcohols, in the preparation of the above mentioned starting materials, intermediates and end products, or in the exchange reactions.

The properties of the compounds according to the invention have been tested in the following test systems.

Firstly the physico-chemical effects of the compounds according to the invention were determined as regards their calcium phosphate crystal formation and precipitation inhibiting activity [Shinoda et al (Calc Tiss Int 1983; 35:87) and Jung et al. (Calc Tiss Res 1973; 11:269] (Table 1).

In addition, the parathyroid hormone stimulated bone resorption inhibition activity in vitro in mouse calvaria, as well as inhibition of retinoid induced bone resorption in thyroparathyroidectomised rats in vivo were determined (Reynolds & Dingle (Calc Tiss Res 1970; 4:339, and Trechsel et al. (J Clin Invest 1987; 80:1679)) (Table 2).

From the tables the superiority of the compounds of the invention, especially their better relative in vivo-antiresorptive activity is apparent.

The partial esters of substituted bisphosphonic acids of the formula I may be used as pharmaceuticals as such, or as their pharmacologically suitable salts, such as the alkali or ammonium salts. Such salts may be prepared by reacting the ester acids with the corresponding inorganic or organic bases. Depending on the reaction conditions, the ester salts may be formed also directly in the above mentioned reactions.

The new compounds I according to this invention may be administered enterally or parenterally. All conventional administration forms, such as tablets, capsules, granules, syrups, solutions, implants and suspensions come into question. Also all adjuvants for manufacture, dissolution and administration of the preparation, as well as stabilizers, viscosity regulating and dispersion agents and buffers, may be used.

Such adjuvants include i.a. tartrate and citrate buffers, alcohols, EDTA and other nontoxic complexing agents, solid and liquid polymers and other sterile substrates, starch, lactose, mannite, methylcellulose, talc, silicic acids, fatty acids, gelatine, agar-agar, calcium phosphate, magnesium stearate, animal and vegetable fats and, if desired, flavouring and sweetening agents.

The dosage depends on several factors, for example on the manner of administration, species, age and individual condition. The daily doses are about 0.1 to 1000 mg, usually 1 to 100 mg per person, and they may be adminstered as a single dose or may be divided into several doses.

In the following, examples of a typical capsule and a tablet are given:

mg/caps.

Capsule

-continued

|  | mg/caps. |
| --- | --- |
| Active ingredient | 10.0 mg |
| Starch | 20.0 mg |
| Magnesium stearate | 1.0 mg |
| Tablet |  |
| Active ingredient | 40.0 mg |
| Microcrystalline cellulose | 20.0 mg |
| Lactose | 67.0 mg |
| Starch | 10.0 mg |
| Talc | 4.0 mg |
| Magnesium stearate | 1.0 mg |

For medicinal use, also an intramuscularly or parenterally administered preparation may be made, for example an infusion concentrate, wherein as adjuvants e.g. sterile water, phosphate buffer, NaCl, NaOH or HCl or other known pharmaceutical adjuvants suitable for the purpose may be used.

The compounds in ester-acid form according to the invention are liquids or waxy substances, usually soluble in organic solvents and in some instances in water. The ester salts are solid, crystalline or typically powdery substances which usually dissolve well in water, in some instances in organic solvents, but only some structure types being poorly soluble in all solvents. The compounds are very stable, also in their neutral solutions at room temperature.

The structure of the compounds may easily be verified with $^1$H-, $^{13}$C- and $^{31}$P-NMR-spectroscopy and FAB-masspectrometry, or when silylated, with EI-masspectrometry. For concentration and impurity determinations 31P-NMR-spectroscopy is very suitable (85% $H_3PO_4$ $\delta=0$). Also for polar compounds as such ion exchange and exclusion-HPLC may be used and for tetraesters and silylated ester acid derivatives GLC or GC/MS may be used. From the compounds sodium and other metals were determined separately as well as the possible crystal water content. From the amine salts, nitrogen was determined.

The following examples illustrate the invention without limiting the same in any way.

Preparation of starting materials

Example A

Preparation of (1-hydroxyethylidene)bisphosphonic acid tetramethyl ester

Dimethylphosphite (0.047 moles) and dibutylamine (0.0026 moles) were dissolved in diisopropylether and to the solution dimethyl acetylphosphonate (0.047 moles) was added at 0° C. The solution was stirred at 0° C. for 4 hours and at room temperature for a day. The product was filtered, washed with diisopropylether and dried. Yield was 8.3 g (67%; 31-P NMR 22.95 ppm; CDCl$_3$).

Dimethyl acetylphosphonate used as the starting material may prepared in the following manner:

To acetyl chloride (0.31 moles) was added at 0° C. slowly trimethylphosphite (0.3 moles). The mixture was stirred for 5 hours at 0° C. and left standing over night at room temperature. The product was distilled at reduced pressure, b.p. 96°–100° C./9 mm Hg. Yield 39 g (86%).

In the corresponding manner may be prepared:

(1-Hydroxyethylidene)bisphosphonic acid P,P-dimethyl P',P'-diethyl ester from dimethyl acetylphosphonate and diethylphosphite (31-P NMR 20.54/23.32 ppm, J=39.4 Hz; CDCl$_3$).

(1-Hydroxyethylidene)bisphosphonic acid P,P-dimethyl P',P'-bis(trimethylsilyl) ester from dimethyl acetylphosphonate and bis(trimethylsilyl)phosphite (31-P NMR 2.89/12.93 ppm, J=44.1 Hz; CDCl$_3$).

(1-Hydroxyethytidene)bisphosphonic acid P,P'-dimethyl P,P'-bis(trimethylsilyl) ester from methyl(trimethylsilyl)acetylphosphonate and methyl(trimethylsilyl)phosphite (31-P NMR −0.50 ppm; CDCl$_3$).

(1-Hydroxypentylidene)bisphosphonic acid P,P-dimethyl P',P'-diethyl ester from dimethyl pentanoylphosphonate and diethylphosphite (31-P NMR 20.9/23.39 ppm, J=37.0 Hz; CDCl$_3$).

(1-Hydroxypentylidene)bisphosphonic acid P,P-dimethyl P',P'-diisopropyl ester from dimethyl pentanoylphosphonate and diisopropylphosphite (31-P NMR 16.63/21.56 ppm, J=41.0 Hz; CDCl$_3$).

(1-Hydroxypentylidene)biphosphonic acid tetramethyl ester from dimethyl pentanoylphosphonate and dimethylphosphite (31-P NMR 20.62 ppm; CDCl$_3$).

(1-Hydroxy-2,2-dimethylpropylidene)bisphosphonic acid tetramethyl ester from dimethyl pivaloylphosphonate and dimethylphosphite (31-P NMR 23.80 ppm; CDCl$_3$).

(1-Hydroxy-2,2-dimethylpropylidene)bisphosphonic acid P,P-dimethyl P',P'-diethyl ester from dimethyl pivaloylphosphonate and diethylphosphite (31-P NMR 20.57/23.46 ppm, J=31.3 Hz; CDCl$_3$).

[Hydroxy(cyclohexyl)methylidene]bisphosphonic acid tetramethyl ester from dimethyl cyclohexanoylphosphonate and dimethylphosphite (31-P NMR 23.13 ppm; CDCl$_3$).

In addition may be prepared:

(1-Hydroxyethylidene) bisphosphonic acid P,P-dimethyl P',P'-diisopropyl ester from diisopropyl acetylphosphonate and dimethylphosphite (31-P NMR 18.69/23.73 ppm, J=40.4 Hz; CDCl$_3$).

(1-Hydroxyethylidene)bisphosphonic acid P,P-diethyl P',P'-diisopropyl ester from diisopropyl acetylphosphonate and diethylphosphite (31-P NMR 16.55/18.95 ppm, J=41.7 Hz; CDCl$_3$).

(1-Hydroxypentylidene)bisphosphonic acid P,P-dimethyl P',P'-diisopropyl ester from diisopropyl pentanoylphosphonate and dimethylphosphite (31-P NMR 16.63/21.56 ppm, J=41.0 Hz; CDCl$_3$).

(1-Hydroxyethylidene)bisphosphonic acid P,P-dimethyl P',P'-dibutyl ester from dibutyl acetylphosphonate and dimethylphosphite (31-P NMR 20.40/23.33 ppm, J=40.1 Hz; CDCl$_3$).

(1-Hydroxypentylidene)bisphosphonicacid P,P-diethyl P',P'-diisopropyl ester from diisopropyl pentanoylphosphonate and diethylphosphite.

[(4-Dimethylamino)-1-hydroxybutylidene]bisphosphonic acid P-ethyl[P,P',P'-tris(trimethylsilyl)] ester from bis(trimethylsilyl)(4-dimethylamino)butanoylphosphonate and ethyl(trimethylsilyl)phosphite.

[(3-methyl(pentyl)amino]-1-hydroxypropylidene]bisphosphonic acid P-methyl [P,P',P'-tris(trimethylsilyl)] ester from methyl(trimethylsilyl)[3-methyl(pentyl)amino]propanoylphosphonate and bis(trimethylsilyl)phosphite.

Example B

Preparation of (1-hydroxypentylidene)bisphosphonic acid tetramethyl ester

A mixture of (1-hydroxypentylidene)bisphosphonic acid (0.1 moles) and trimethyl ortoformiate (0.5 moles) was heated for 6 hours at 100° C. Thereafter the methanol formed in the reaction and unreacted ortoformiate was distilled off. The residue was the tetramethyl ester, yield 25 g (82%, 31-P NMR 20.62 ppm; CDCl$_3$).

In the same manner may be prepared:

(1-Hydroxyethylidene)bisphosphonic acid tetramethyl ester (31-P NMR 22.95 ppm; CDCl$_3$).

(1-Hydroxy-2,2-dimethylpropylidene)bisphosphonic acid tetramethyl ester (31-P NMR 23.80 ppm; CDCl$_3$).

(4-Amino-1-hydroxybutylidene)bisphosphonic acid tetramethyl ester.

(3-Amino-1-hydroxypropylidene)bisphosphonic acid tetramethyl ester.

(3-Amino-1-hydroxypropylidene)bisphosphonic acid tetraethyl ester.

[3-(Dimethylamino)-1-hydroxypropylidene]bisphosphonic acid tetramethyl ester.

(6-Amino-1-hydroxyhexylidene)bisphosphonic acid tetraethyl ester (31-P NMR 23.1 ppm; CDCl$_3$).

(6-Amino-1-hydroxyhexylidene)bisphosphonic acid tetramethyl ester.

[3-(Dimethylamino)-1-hydroxypropylidene]bisphosphonic acid tetraethyl ester.

[(3-Benzyloxycarbonylamino)-1-hydroxypropylidene]bisphosphonic acid tetramethyl ester.

[(4-Benzyloxycarbonylamino)-1-hydroxybutylidene]-bisphosphonic acid tetraethyl ester.

Example C

Preparation of (1-hydroxy-2,2-dimethylpropylidene)-bisphosphonic acid tetramethyl ester Into a chloroform solution of trimethyl phosphite (0.1 moles) and dimethyl phosphite (0.1 moles) pivaloyl chloride (0.1 moles) dissolved in chloroform was added slowly at 0° C. The mixture was heated at 80° C. for 10 hours. The solvent was evaporated at reduced pressure, and the product precipitated by adding diisopropylether. Yield 24 g (80%, 31-P NMR 23.80 ppm; CDCl$_3$).

In the same manner may be prepared

[4-(N-phtalimidyl)-1-hydroxybutylidene]bisphosphonic acid tetramethyl ester (31-P NMR 19.90 ppm; CDCl$_3$).

[3-(N-phtalimidyl)-1-hydroxypropylidene]bisphosphonic acid tetraethyl ester.

[3-(Benzyloxycarbonylamino)-1-hydroxypropylidene]bisphosphonic acid tetramethyl ester.

EXAMPLE 1

Preparation of (1-hydroxyethylidene)bisphosphonic acid P',P'-diisopropyl ester and its disodium salt Into a acetonitrile solution of (1-hydroxyethylidene)-bisphosphonic acid P,P-dimethyl P',P'-diisopropyl ester (0.02 moles) and sodium iodide (0.04 moles) chlorotrimethylsilane (0.042 moles) was added slowly at room temperature. The solution was stirred for 2 hours, whereafter the solvent was evaporated at reduced pressure. The evaporation residue was dissolved in a small amount of warm water, and the solution was made alkaline with a dilute sodium hydroxide solution. The product was precipitated by adding ethanol (31-P NMR 16.80/23.24 ppm, J=37.6 Hz; D$_2$O).

In a corresponding manner the following esters and their sodium salts may be prepared:

(1-Hydroxyethylidene)bisphosphonic acid P,P-dimethyl ester from the corresponding tetramethyl ester (31-P NMR 13.25/32.20 ppm, J=29.0 Hz; D$_2$O).

(1-Hydroxyethylidene)bisphosphonic acid P',P'-dibutyl ester from the corresponding P,P-dimethyl P',P'-dibutyl ester (31-P NMR 27.95/28.97 ppm, J=31,2 Hz; D$_2$O).

(1-Hydroxyethylidene)bisphosphonic acid P',P'-diethyl ester from the corresponding P,P-dimethyl P',P'-diethyl ester (31-P NMR 13.41/29.68 ppm, J=29.9 Hz; D$_2$O).

(4-Amino-1-hydroxybutylidene)bisphosphonic P,P-dimethyl ester from the corresponding tetramethylester.

(6-Amino-1-hydroxyhexylidene)bisphosphonic acid P,P-dimethyl ester from the corresponding tetramethyl ester.

[4-(N-Phtalimidyl)-1-hydroxybutylidene]-bisphosphonic acid P,P-dimethyl ester from the corresponding tetramethyl ester (31-P NMR 15.76/23.8 ppm, J=23.7 Hz; D$_2$O).

(3-Amino-1-hydroxypropylidene)bisphosphonic acid P,P-diethyl ester from the corresponding tetraethyl ester.

(3-Amino-1-hydroxypropylidene)bisphosphonic acid P,P-dimethyl ester from the corresponding tetramethyl ester.

(1-Hydroxypentylidene)bisphosphonic acid P',P'-diisopropyl ester from the corresponding P,P-dimethyl P',P'-diisopropyl ester (31-P NMR 14.60/26.80 ppm, J=31.7 Hz; D$_2$O).

(1-Hydroxypentylidene)bisphosphonic acid P,P-dimethyl ester from the corresponding tetramethyl ester (31-P NMR 15.72/27.62 ppm, J=31.0 Hz; D$_2$O).

(1-Hydroxypentylidene)bisphosphonic acid P',P'-diethyl ester from the corresponding P,P-dimethyl P',P'-diethyl ester (31-P NMR 12.30/28.70 ppm, J=27.1 Hz; D$_2$O).

(1-Hydroxy-1-cyclohexylmethylidene)bisphosphonic acid P,P-dimethyl ester from the corresponding tetramethyl ester.

EXAMPLE 2

Preparation of (1-hydroxypentylidene)bisphosphonic acid monoisopropyl ester

The P,P-dimethyl P',P'-diisopropyl ester of (1-hydroxypentylidene)bisphosphonic acid (0.02 moles) was dissolved in dichloromethane and to the solution was added slowly at room temperature bromotrimethylsilane (0.062 moles). The solution was mixed at room temperature for 3 hours, whereafter the solvent was evaporated at reduced pressure. The evaporation residue was dissolved in a small amount of methanol, and the solution was evaporated (31-P NMR 17.72/22.76 ppm, J=27.1 Hz; D$_2$O).

In the same manner may be prepared:

(1-Hydroxyethylidene)bisphosphonic acid monoisopropyl ester from the corresponding P,P-dimethyl P',P'-diisopropyl ester (31-P NMR 18.36/23.04 ppm, J=28.8 Hz; D$_2$O).

(1-Hydroxyethylidene) bisphosphonic acid monoisopropyl ester from the corresponding tetraisopropyl ester.

(1-Hydroxyethylidene)bisphosphonic acid monobutyl ester from the corresponding P,P-dimethyl P',P'-dibutyl ester (31-P NMR 18.17/22.80 ppm, J=29.6 Hz; D$_2$O).

(4-Amino-1-hydroxybutylidene)bisphosphonic acid monomethyl ester from the corresponding tetramethyl ester.

[4-(N-Phtalimidyl)-1-hydroxybutylidene]bisphosphonic acid monomethyl ester from the corresponding tetramethyl ester.

(1-Hydroxypentylidene)bisphosphonic acid monomethyl ester from the corresponding tetramethyl ester (31-P NMR 16.36/24.0 ppm, J=24.5 Hz; $D_2O$).

[Hydroxy(cyclohexyl)methylidene]bisphosphonic acid monomethyl ester from the corresponding tetramethyl ester (31-P NMR 15.84/23.40 ppm, J=27.0 Hz; $D_2O$).

(1-Hydroxypentylidene)bisphosphonic acid monoethyl ester from the corresponding P,P-dimethyl P',P'-diethyl ester (31-P NMR 18.73/20.61 ppm, J=32.3 Hz; $D_2O$).

(1-Hydroxy-2,2-dimethylpropylidene)bisphosphonic acid monomethyl ester from the corresponding tetramethyl ester (31-P NMR 16.55/24.18 ppm, J=23.3 Hz; $D_2O$).

[3-(Benxyloxycarbonylamino)-1-hydroxypropylidene]bisphosphonic acid monoethylester from the corresponding tetraethyl ester.

[3-(N-phtalimidyl)-1-hydroxypropylidene]bisphosphonic acid monomethyl ester from the corresponding tetramethyl ester.

EXAMPLE 3

Preparation of (1-hydroxyethylidene)bisphosphonic acid trimethyl ester and its sodium salt The tetramethyl ester of (1-hydroxyethylidene)bisphosphonic acid (0.02 moles) was dissolved in acetonitrile, and to the solution was slowly added chloro(tert-butyl)(dimethyl)silane (0.022 moles) dissolved in acetonitrile. The solution was mixed at 60° C. for 4 hours. The solvent was evaporated and the evaporation residue was dissolved in a small amount of water. The solution was made alkaline with a dilute sodium hydroxide solution, and the product precipitated by adding ethanol (31-P NMR 16.89/28.41 ppm, J=34.8 Hz; $D_2O$).

In a corresponding manner may be prepared (1-Hydroxypentylidene)bisphosphonic acid trimethyl ester from the corresponding tetramethyl ester (31-P NMR 12.12/31.38 ppm, J=26.0 Hz; $D_2O$).

(1-Hydroxy-2,2-dimethylpropylidene)bisphosphonic acid trimethyl ester from the corresponding tetramethyl ester.

[3-(N-Phtalimidyl)-1-hydroxypropylidene]bisphosphonic acid trimethyl ester from the corresponding tetramethyl ester.

[4-(Benxyloxycarbonylamino)-1-hydroxybutylidene]-bisphosphonic acid trimethyl ester from the corresponding tetramethyl ester.

By using the double amount of chloro(tert-butyl)(dimethyl)silane (0.044 moles) one can prepare (1-Hydroxyethylidene)bisphosphonic acid P,P'-dimethyl ester from the corresponding tetramethyl ester (31-P NMR 21.19 ppm; $D_2O$).

(1-Hydroxypentylidene)bisphosphonic acid P,P'-dimethyl ester from the corresponding tetramethyl ester (31-P NMR 20.70 ppm; $D_2O$).

[4-(N-phtalimidyl)-1-hydroxybutylidene]bisphosphonic acid P,P'-dimethyl ester from the corresponding tetramethyl ester (31-P NMR 18.78 ppm; $D_2O$).

[3-(Benzyloxycarbonylamino)-1-hydroxypropylidene]bisphosphonic acid P,P'-diethyl ester from the corresponding tetraethyl ester.

Further, in a manner corresponding to the previous example the following compounds may be prepared by using instead of chloro(tert-butyl)(dimethyl)silane for example bromo(trimethyl)silane (1 equivalent):

(1-Hydroxyethylidene)bisphosphonic acid P-methyl P',P'-dibutyl ester from the corresponding P,P-dimethyl P',P'-dibutyl ester (31-P NMR 17.19/25.79 ppm, J=34.7 Hz; $D_2O$).

(1-Hydroxyethylidene)bisphosphonic acid P-methyl P',P'-diethyl ester from the corresponding P,P-dimethyl P',P'-diethyl ester (31-P NMR 17.47/26.01 ppm, J=35.1 Hz; $D_2O$).

(1-Hydroxyethylidene)bisphosphonic acid P-methyl P',P'-diisopropyl ester from the corresponding P,P-dimethyl P',P'-diisopropyl ester (31-P NMR 19.10/22.44 ppm, J=37.3 Hz; $D_2O$).

(1-Hydroxypentylidene)bisphosphonic acid P-methyl P',P'-diethyl ester from the corresponding P,P-dimethyl P',P'-diethyl ester.

[4-(N-Phtalimidyl)-1-hydroxybutylidene)bisphosphonic acid trimethyl ester from the corresponding tetramethyl ester (31-P NMR 12.01/30.89 ppm J=25.3 Hz; $D_2O$).

(6-Amino-1-hydroxyhexylidene)bisphosphonic acid trimethylester from the corresponding tetramethyl ester.

EXAMPLE 4

Preparation of (1-hydroxyethylidene)bisphosphonic acid monomethyl ester and its trisodium salt A toluene solution of (1-hydroxyethylidene)bisphosphonic acid (0.02 moles) and trimethyl ortoformiate (0.04 moles) was mixed at 100° C. for 4 hours. The solvent and unreacted triethyl ortoformiate was evaporated under reduced pressure. The evaporation residue was dissolved in ethanol. When a calculated amount (0.06 moles) of a 40% sodium hydroxide solution was added into the ethanol solution, the product precipitated as the trisodium salt (31-P NMR 17.25/24.86 ppm, J=27.3 Hz; $D_2O$).

In a corresponding manner may be prepared (3-Amino-1-hydroxypropylidene)bisphosphonic acid monoethyl ester (6-Amino-1-hydroxyhexylidene)bisphosphonic acid monomethyl ester.

EXAMPLE 5

Preparation of (1-hydroxypentylidene)bisphosphonic acid monomethyl ester and its trisodium salt The tetramethyl ester of (1-hydroxypentylidene)bisphosphonic acid (0.01 moles) was dissolved in toluene (70 ml) and to the solution methanesulphonic acid (0.06 moles) was added. The solution was stirred while heating, and the progress of hydrolysis was followed with $^{31}P$ NMR. The mixture was cooled and the solvent evaporated under reduced pressure. The evaporation residue was dissolved in a dilute sodium hydroxide solution. To the solution the double volume of ethanol was added and the solution was cooled. The precipitated product was filtered and dried (yield 52%, 31-P NMR 16.36/24.00 ppm, J=24.5 Hz; $D_2O$).

EXAMPLE 6

Preparation of (1-hydroxyethylidene)bisphosphonic acid P,P'-dimethyl ester (1-Hydroxyethylidene)bisphosphonic acid P,P'-dimethyl P,P'-bis-trimethylsilyl ester (0.01 moles) was dissolved in methanol and the solution mixed at room temperature for 2 hours. The solvent was evaporated, the evaporation residue was dissolved in a dilute sodium hydroxide solution and the disodium salt of the product was precipitated by adding a double volume of ethanol (yield 72%, 31-P NMR 21.19 ppm; D$_2$O).

EXAMPLE 7

Preparation of (1-hydroxypentylidene)bisphosphonic acid P,P'-dimethyl ester

The tetramethyl ester of (1-hydroxypentylidene)bisphosphonic acid (0.01 moles) was dissolved in acetone, and to the solution sodium iodide (0.023 moles) was added. The solution was mixed at room temperature for 8 hours, whereafter it was filtered. The solvent has evaporated. The product was isolated from the evaporation residue as the disodium salt as has been described in the previous example (yield 59%, 31-P NMR 19.06 ppm; D$_2$O).

In a corresponding manner may be prepared (1-Hydroxy-2,2-dimethylpropylidene)bisphosphonic acid P,P'-dimethyl ester from the corresponding tetramethyl ester (31-P NMR 20.33 ppm; D$_2$O).

[Hydroxy(cyclohexyl)methylidene]bisphosphonic acid P,P'-dimethyl ester from the corresponding tetramethyl ester (31-P NMR 18.79 ppm; D$_2$O).

(1-Hydroxypentylidene)bisphosphonic acid P-methyl P'-ethyl ester from the corresponding P,P-dimethyl P',P'-diethyl ester (31-P NMR 19.06 ppm; D$_2$O).

[4-(Benzyloxycarbonylamino)-1-hydroxybutylidene]-bisphosphonic acid P,P'-diethyl ester from the corresponding tetraethyl ester.

[4-(Benzyloxycarbonylamino)-1-hydroxybutylidene]-bisphosphonic acid P,P'-dimethyl ester from the corresponding tetramethyl ester.

[3-(Benzyloxycarbonylamino)-1-hydroxypropylidene]bisphosphonic acid P,P'-diethyl ester from the corresponding tetraethyl ester.

[3-(Benzyloxycarbonylamino)-1-hydroxypropylidene]bisphosphonic acid P,P'-dimethyl ester from the corresponding tetramethyl ester.

EXAMPLE 8

Preparation of (1-hydroxyethylidene)bisphosphonic acid monomethyl ester

Finely ground (1-hydroxyethylidene)bisphosphonic acid (0.005 moles) was mixed with 100 ml of chloroform and to the mixture 25 ml of an appr. 2% ether solution of diazomethane were slowly added at room temperature. After the addition, the mixing was continued for 1 hour, whereafter the solution was evaporated at reduced pressure (yield 42%, 31-P NMR 17.25/24.84 ppm, J=27.3; D$_2$O).

In a corresponding manner other mono- and diesters, for example dimethyl, mono- and diethyl and benzyl esters may be prepared by using suitable diazo reagents.

EXAMPLE 9

Preparation of (1-hydroxypentylidene)bisphosphonic acid monomethyl ester and its trisodium salt The tetramethyl ester of (1-hydroxypentylidene)bisphosphonic acid (0.01 moles) was slurried in a 10% hydrochloric acid solution and the solution mixed at 70° C. The progress of the reaction was followed using 31-P NMR. After the reaction, the mixture was evaporated to dryness, the evaporation residue dissolved in a sodium hydroxide solution and the product precipitated by adding ethanol. The product was filtered and dried (yield 55%, 31-P NMR 16.36/24.00 ppm, J=24.5 Hz; D$_2$O).

In a corresponding manner [(3-dimethylamino)-1-hydroxypropylidene]bisphosphonic acid monomethyl ester may be prepared.

EXAMPLE 10

Preparation of (4-amino-1-hydroxybutylidene)bisphosphonic acid P,P-diethyl ester disodium salt

[4-(Benzyloxycarbonylamino)-1-hydroxybutylidene]-bisphosphonic acid P,P-diethyl ester (1 g) was dissolved in ethanol (30 ml) and hydrogenated at a pressure of 35 psi using as a catalyst 5% palladium-carbon (0.1 g). The catalyst was filtered off and the pH of the filtrate was adjusted to pH 7-7.5 with a dilute sodium hydroxide solution. The solution was evaporated and the evaporation residue was treated with acetone. The product was filtered and dried (yield 65%).

In the same manner may be prepared (3-Amino-1-hydroxypropylidene)bisphosphonic acid P,P'-dimethyl ester from [3-(benzyloxycarbonylamino)-1-hydroxypropylidene]bisphosphonic acid P,P'-dimethyl ester.

(3-Amino-1-hydroxypropylidene)bisphosphonic acid P,P'-diethyl ester from [3-(benzyloxycarbonylamino)-1-hydroxypropylidene]bisphosphonic acid P,P'-diethyl ester.

(4-Amino-1-hydroxybutylidene)bisphosphonic acid P,P'-dimethyl ester from [4-(benzyloxycarbonylamino)-1-hydroxybutylidene]bisphosphonic acid P,P'-dimethyl ester.

EXAMPLE 11

Preparation of [(4-dimethylamino)-1-hydroxybutylidene]bisphosphonic acid monoethyl ester and its trisodium salt A mixture of [(4-dimethylamino)-1-hydroxybutylidene]bisphosphonic acid P-ethyl [P,P',P'-tris(-trimethylsilyl)] ester (0.01 moles) and dilute hydrochloric acid was stirred at 0° C. for 0.5 hours. To the filtered solution dilute sodium hydroxide was added (in excess 0.02 moles) and the product was precipitated with ethanol.

In a corresponding manner [[(3-methyl(pentyl)amino]-1-hydroxypropylidene]bisphosphonic acid monomethyl ester may be prepared.

We claim:

1. Pharmaceutical composition characterized in that it has as the active agent a compound having the formula I

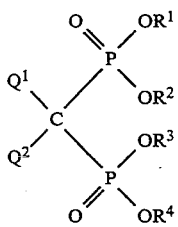

wherein one of the groups R$_1$-R$_4$ is selected from the group consisting of methyl, ethyl and isopropyl, the remaining groups being hydrogen; and wherein Q$^1$ is hydroxy and Q$^2$ is selected from the group consisting of methyl, ethyl, propyl, isopropyl, 2,2-dimethylpropyl, 1,1-dimethylethyl, butyl, cyclohexyl, 2-hydroxyethyl, 3-hydroxypropyl, 2-aminoethyl, 3-aminopropyl, (3-dimethylamino)- propyl, [3-methyl(pentyl) amino]propyl, [2-methyl[pentyl)amino]ethyl, and 5-aminopentyl.

2. A composition according to the claim 1 wherein the active agent is selected from the group consisting of (1-hydroxyethylidene)bisphosphonic acid monomethyl and monoethyl ester, (1-hydroxypentylidene)bisphosphonic acid monomethyl ester, (2,2-dimethyl-1-hydroxypropylidene)bisphosphonic acid monomethyl ester, [hydroxy(cyclohexyl)methylidene]bisphosphonic acid monomethyl ester, (1,3-dihydroxypropylidene)bisphosphonic acid monoethyl ester, (3-amino-1-hydroxypropylidene)bisphosphonic acid monomethyl and monoethyl ester, (4-amino-1-hydroxybutylidene)bisphosphonic acid monomethyl and monoethyl ester, (6-amino-1-hydroxyhexylidene)bisphosphonic acid monomethyl- and monoisopropyl ester, [(4-dimethylamino)-1-hydroxybutylidene]bisphosphonic acid monoethyl ester, [(3-methyl(pentyl)amino]-1-hydroxypropylidene]bisphosphonic acid monomethyl ester.

3. A method of treating a physiological disorder relating to the metabolism of calcium or other divalent metals, or to (pyro)phosphate functions, by administering to a patient a pharmacological composition characterized in that it has as an active agent a compound having the formula I

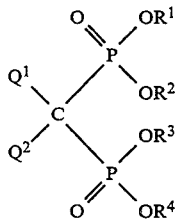

wherein one of the groups $R_1$–$R_4$ is selected from the group consisting of methyl, ethyl and isopropyl, the remaining groups being hydrogen; and
wherein $Q^1$ is hydroxy and $Q^2$ is selected from the group consisting of methyl, ethyl, propyl, isopropyl, 2,2-dimethylpropyl, 1,1-dimethylethyl, butyl, cyclohexyl, 2-hydroxyethyl, 3-hydroxypropyl, 2-aminoethyl, 3-aminopropyl, (3-dimethylamino)propyl, [3-methyl(pentyl)amino]propyl, [2-methyl[pentyl)amino]ethyl, and 5-aminopentyl.

4. The method of claim 3, wherein the active agent is selected from the group consisting of:
(1-hydroxyethylidene)bisphosphonic acid monomethyl and monoethyl ester,
(1-hydroxypentylidene)bisphosphonic acid monomethyl ester,
(2,2-dimethyl-1-hydroxypropylidene)bisphosphonic acid monomethyl ester,
[hydroxy(cyclohexyl)methylidene]bisphosphonic acid monomethyl ester,
(1,3-dihydroxypropylidene)bisphosphonic acid monoethyl ester,
(3-amino-1-hydroxypropylidene)bisphosphonic acid monomethyl and monoethyl ester,
(4-amino-1-hydroxybutylidene)bisphosphonic acid monomethyl and monoethyl ester,
(6-amino-1-hydroxyhexylidene)bisphosphonic acid monomethyl- and monoisopropyl ester,
(4-dimethylamino)-1-hydroxybutylidene]bisphosphonic acid monoethyl ester,
[(3-methyl(pentyl)amino]-1-hydroxypropylidene]bisphosphonic acid monomethyl ester.

* * * * *